United States Patent
Surujballi et al.

(10) Patent No.: US 7,018,616 B2
(45) Date of Patent: Mar. 28, 2006

(54) RAPID SEROLOGICAL TEST FOR PARATUBERCULOSIS USING FLUORESCENCE POLARIZATION TECHNOLOGY

(75) Inventors: Om P. Surujballi, Nepean (CA); Kathryn Irene Stilwell, Woodlawn (CA)

(73) Assignees: Diachemix LLC, Milwaukee, WI (US); Her Majesty the Queen in Right of Canada as represented by the Canadian Food Inspection Agency, Ottawa (CA)

(*) Notice: Subject to any disclaimer, the term of this patent is extended or adjusted under 35 U.S.C. 154(b) by 0 days.

(21) Appl. No.: 10/493,095

(22) PCT Filed: Oct. 31, 2002

(86) PCT No.: PCT/US02/35002

§ 371 (c)(1),
(2), (4) Date: Apr. 19, 2004

(87) PCT Pub. No.: WO03/037369

PCT Pub. Date: May 8, 2003

(65) Prior Publication Data

US 2004/0191795 A1    Sep. 30, 2004

Related U.S. Application Data

(60) Provisional application No. 60/335,253, filed on Oct. 31, 2001.

(51) Int. Cl.
*A61K 49/00* (2006.01)
*A61K 39/04* (2006.01)
*C12Q 1/00* (2006.01)
*G01N 33/566* (2006.01)

(52) U.S. Cl. ............ 424/9.1; 424/9.2; 424/130.1; 424/139.1; 424/150.1; 424/164.1; 424/184.1; 424/248.1; 435/4; 435/7.1; 436/501; 436/543; 436/546

(58) Field of Classification Search ............ 424/9.1, 424/9.2, 130.1, 139.1, 150.1, 164.1, 184.1, 424/248.1; 435/4, 7.1; 436/501, 543, 546
See application file for complete search history.

(56) References Cited

U.S. PATENT DOCUMENTS 5,976,820 A * 11/1999 Jolley et al. .......... 435/7.32
6,110,750 A    8/2000 Sugden et al.
6,387,372 B1    5/2002 Cocito et al.
6,596,546 B1    7/2003 Jolley et al.

OTHER PUBLICATIONS

Sugden, et al., "Lipoarabinomannan and Lipid-Free Arabinomannan Antigens of *Mycobacterium paratuberculosis*," *Infection and Immunity*, vol. 55, No. 3, Mar. 1987, p. 762-770.
Lin, et al., "Modification of the *Mycobacterium bovis*Extracellular Protein MPB70 with Fluorescein for Rapid Detection of Specific Serum Antibodies by Fluorescence Polarization," *Clinical and Diagnostic Laboratory Immunology*, vol. 3, No. 4, Jul. 1996, p. 438-443.
Nasir, et al., "Fluorescence Polarization: An Analytical Tool for Immunoassay and Drug Discovery," *Combinatorial Chemistry & High Throughput Screening*, 1999, 2, 177-190.
International Search Report, International application No. PCT/US02/35002, Mar. 14, 2003.
Written Opinion, International application No. PCT/US02/35002, Sep. 24, 2004.
Koets et al., "Differential Changes in Heat Shock Protein-, Lipoarabinamannan-, and Purified Protein Dervative-Specific Immunoglobulin G1 and G2 Isotype Responses during Bovine *Mycobacterium avium* subsp. *paratuberculosis* Infection," Infection and Immunity, vol. 69, no. 3, pp. 1492-1498 (Mar. 2001).

* cited by examiner

*Primary Examiner*—Rodney P Swartz
(74) *Attorney, Agent, or Firm*—McDonnell Boehnen Hulbert & Berghoff LLP

(57) ABSTRACT

The present invention provides an assay for detection of serum antibodies to *M. paratuberculosis*. A tracer, comprising a carbohydrate antigen isolated from *M. paratuberculosis* that is conjugated to a fluorophore, is added to a serum sample from an animal to form a mixture. The fluorescence polarization of the mixture is then measured. The presence of serum antibodies to *M. paratuberculosis* is indicated by a fluorescence polarization value of the mixture that is higher than the fluorescence polarization value of a control. The present invention further provides a tracer for use in a fluorescence polarization assay for antibodies specific for *M. paratuberculosis*. The tracer comprises a carbohydrate antigen isolated from *M. paratuberculosis* and conjugated to a fluorophore, such that the tracer is able to bind to antibodies specific for *M. paratuberculosis* to produce a detectable change in fluorescence polarization.

7 Claims, No Drawings

RAPID SEROLOGICAL TEST FOR PARATUBERCULOSIS USING FLUORESCENCE POLARIZATION TECHNOLOGY

CROSS REFERENCE TO RELATED APPLICATIONS

This application claims priority from U.S. Patent App. No. 60/335,253, filed 31 Oct. 2001. All patents, patent applications, as well as all other scientific and/or technical writings referred to herein are incorporated by reference to the extent that they are not contradictory.

BACKGROUND OF THE INVENTION

1. Field of the Invention

This invention relates to the field of diagnostic assays. More particularly, this invention relates to a homogeneous assay that uses fluorescence polarization technology for the detection of antibodies to *Mycobacterium paratuberculosis* in bovine sera.

2. Description of Related Art

Currently, ELISA methods are used to detect *Mycobacterium paratuberculosis* infection in animals, such as cattle. However, there are a number of disadvantages associated with ELISA techniques. For example, ELISA methods are undesirably labor intensive, in that they typically involve several washings, liquid transfers, and incubation times.

Accordingly, there is a need in the art for a serological test for *M. paratuberculosis* that is rapid and easy to perform.

SUMMARY OF THE INVENTION

In a first principal aspect, the present invention provides an assay for detection of serum antibodies to *M. paratuberculosis*. A tracer, comprising a fluorophore conjugated to an antigen isolated from *M. paratuberculosis*, is added to a serum sample from an animal to form a mixture. The fluorescence polarization of the mixture is then measured. The presence of serum antibodies to *M. paratuberculosis* is determined from the measured fluorescence polarization of the mixture, e.g., that it is higher than that of a control. The tracer can be a carbohydrate antigen isolated from *M. paratuberculosis*.

In a second principal aspect, the present invention provides a tracer for use in a fluorescence polarization assay for antibodies specific for *M. paratuberculosis*. The tracer can comprise a carbohydrate antigen isolated from *M. paratuberculosis*. The tracer is conjugated to a fluorophore, such that the tracer is able to bind to antibodies specific for *M. paratuberculosis* to produce a detectable change in fluorescence polarization.

DETAILED DESCRIPTION OF THE INVENTION

This assay utilizes an antigen that has been purified from *M. paratuberculosis* and subsequently labeled with a fluorophore. The antigen can be a carbohydrate antigen. To perform this assay, serum is diluted in phosphate buffered saline (PBS) supplemented with 0.1% sodium azide and 0.05% lithium dodecyl sulfate (PBSALDS), and a baseline reading is obtained in a fluorescence polarization analyzer (FPM-1, Diachemix Corporation). The fluorescently-labeled antigen is then added to the test tube containing the diluted serum and the fluorescence polarization reading is obtained. The presence of antibody specific to *M. paratuberculosis* is indicated by a fluorescence polarization value that is higher than that obtained with a diluent buffer or a known negative serum control.

Compared to the ELISA, this assay is rapid, and technically simple to perform since it requires the addition of only a single reagent, and does not involve any separation or washing steps. Typically, results are obtained in minutes.

EXAMPLE 1

Culture Conditions

*Mycobacterium paratuberculosis*, Strains II, II, IV, V, C286 and C300 (culture collection of Animal Diseases Research Institute, Nepean, Ontario, Canada) were each grown in Reids medium and in Longs medium for 7 to 10 days at 37° C. The seed culture grown in Longs medium was then used to inoculate multiple 1 liter flasks containing 500 mL of Longs medium and the seed culture grown on Reids medium was used to inoculate multiple 1 liter flasks containing 500 mL of Reids medium. The flasks were then incubated at 37° C. for 90 days.

EXAMPLE 2

Preparation of Labeled Antigen

The 90-day cultures of all of the strains of *M. paratuberculosis* described, grown in both media, were pooled in a glass bottle and the mixture was adjusted to pH 8 using 4 N sodium hydroxide. This mixture was stored at 4° C. for 2 weeks with shaking every 2 to 3 days. The mixture was then autoclaved for 3 hours in flowing steam after which the bottle was left undisturbed for 2 days to allow the cells to settle to the bottom. The fluid was then siphoned, after which the cells were filtered through sterile Whatman #2 paper. The cells were then dried, weighed, and stored at −20° C. Aliquots of cells were thawed overnight at 4° C. and water was added to make a slurry. Liquid phenol (90%) was then added to the slurry to yield a final phenol concentration of 30.3% (vol/vol). The slurry was next homogenized with a Polytron Homogenizer fitted with a PT 20 probe (Bricann Instruments, Ontario, Canada) for 2 minutes at room temperature. The homogenate was stirred at room temperature for 30 minutes and then centrifuged (30,000×g, for 30 minutes at 4° C.) using a swinging bucket rotor. After centrifugation, most of the aqueous phase from each tube was aspirated with a Pasteur pipette and pooled. Water (5 ml) was then added to each tube and mixed gently with the remaining aqueous phase. The tubes were re-centrifuged as before, the aqueous phase removed and pooled with the first aqueous phase extract. The pool of the aqueous phase extracts was then dialyzed (3000 kdalton molecular weight cut off) against tap water for 24 hours and then against distilled water for a further 48 hours. The extract was then concentrated approximately 15-fold with an Amicon Ultrafiltration Cell (Millipore, Ottawa, Canada) fitted with an Amicon YM-1 membrane (Millipore). An aliquot (600 µl) of this extract was mixed with 1M sodium hydroxide (60 µl) and incubated at 37° C. for 1 hour. The mixture was then added to 2 ml of Polymixin B agarose (Sigma-Aldrich Canada Limited, Oakville, Ontario, Canada), which was washed prior to use with phosphate buffered saline (PBS, 0.01M sodium phosphate +0.85% sodium chloride, pH 7.2). The Polymixin B agarose-antigen mixture was incubated at 37° C. for 2 hours. The mixture was then centrifuged (15,000×g, for 2 minutes) and the supernatant was removed. The supernatant (approximately 600 μl) was added to 1.2 mg of fluorescein isothiocyanate Isomer I (FITC, Sigma) and incubated at 37° C. for 1 hour. The labeled antigen was then added to a Sephadex G-25 Pine (Pharmacia, Baie D'Urfe, Quebec, Canada) column (1×25 cm) pre-equilibrated with 0.1 M sodium phosphate buffer pH 7.0. The FITC-labeled antigen was then separated from the free FITC by elution with the 0.1M phosphate buffer. The fractions were monitored at a wavelength of 492 nm. Two peaks were obtained and fractions in the first peak were pooled and used as the labeled antigen in the fluorescence polarization assay for detection of antibodies specific to *M. paratuberculosis.*

EXAMPLE 3

Procedure for Performing the Fluorescence Polarization Assay

Bovine serum was diluted 1:25 in PBS supplemented with 0.1% sodium azide (Sigma) and 0.05% lithium dodecyl sulfate (Sigma) (PBSALDS). A baseline reading was then obtained in a Fluorescence Polarization Analyzer (FPM-1, Diachemix Corporation, Grayslake, Ill.). An aliquot of FITC-labeled antigen (which was pre-determined to yield a total intensity value of approximately 300,000) was then added to the diluted serum. The fluorescence polarization reading was then obtained. It was found that the presence of specific antibody gave a fluorescence polarization value higher than that obtained with a diluent buffer or a known negative serum control.

EXAMPLE 4

Detection of *M. paratuberculosis* Antibodies in Infected Animals

Sera from over a thousand *M. paratuberculosis*-infected and non-infected cattle were obtained by procedures known in the art The sera were tested for *M. paratuberculosis* antibodies using the tracer prepared as described above in the fluorescence polarization assay described above. The sera were also tested for *M. paratuberculosis* antibodies using an ELISA assay.

The ELISA method detected 23 *M. paratuberculosis*-infected sera; the fluorescence polarization method detected 20 of those 23 *M. paratuberculosis*-infected sera. Thus, the relative sensitivity of the fluorescence polarization method was about 87%.

1013 sera tested negative using the ELISA method; 1003 of those 1013 non-infected sera also tested negative using the fluorescence polarization method. Thus, the relative specificity of the fluorescence polarization method was about 99%

The foregoing description of the invention is presented for purposes of illustration and description, and is not intended, nor should be construed, to be exhaustive or to limit the invention to the precise forms disclosed. The description was selected to best explain the principles of the invention and practical application of these principles to enable others skilled in the art to best utilize the invention in various embodiments and with various modifications as are suited to the particular use contemplated. It is intended that the scope of the invention not be limited by the specification, but defined by the claims.

We claim:

1. A method for detecting antibodies to *M. paratuberculosis*, the method comprising:

adding a tracer to a sample from an animal to form a mixture, wherein the tracer comprises a fluorophore conjugated to an antigen isolated from the aqueous phase of a phenol-water extraction of *M. paratuberculosis* cells;

measuring the fluorescence polarization of the mixture;

measuring the fluorescence polarization of a control;

comparing the fluorescence polarization of the mixture with the fluorescence polarization of the control; and detecting the presence of antibodies to *M. paratuberculosis* in the mixture from the measured fluorescence polarization of the mixture.

2. The method of claim 1, wherein the sample is serum.

3. The method of claim 1, wherein the fluorophore is fluorescein isothiocyanate.

4. A tracer for detecting *M. paratuberculosis* infected sera in a fluorescence polarization assay, the tracer comprising:

a fluorophore conjugated to an antigen isolated from *M. paratuberculosis* by:

(a) growing cultures of *M. paratuberculosis;*

(b) recovering *M. paratuberculosis* cells from the culture;

(c) adding liquid phenol to the cells to form a mixture;

(d) homogenizing the mixture;

(e) isolating the aqueous phase from the homogenized mixture;

(f) dialyzing the aqueous phase;

(g) concentrating the aqueous phase;

(h) adding sodium hydroxide to the aqueous phase;

(i) adding polymyxin B agarose to the aqueous phase;

(j) removing the polymyxin B agarose from the aqueous phase; and (k) recovering the aqueous phase containing the antigen.

5. The tracer of claim 4, wherein the tracer comprises a fluorophore conjugated to a carbohydrate antigen isolated from *M. paratuberculosis.*

6. The tracer of claim 5, wherein the fluorophore is fluorescein isothiocyanate.

7. A kit for detecting *M. paratuberculosis* infected sera by fluorescence polarization, wherein the kit comprises a tracer as in claim 4.

* * * * *